(12) United States Patent
Hagiwara

(10) Patent No.: US 7,519,144 B2
(45) Date of Patent: Apr. 14, 2009

(54) MULTI-POSITIONAL CT IMAGE PRODUCING METHOD AND X-RAY CT APPARATUS

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 390 days.

(21) Appl. No.: 11/017,014

(22) Filed: Dec. 20, 2004

(65) Prior Publication Data

US 2005/0135549 A1   Jun. 23, 2005

(30) Foreign Application Priority Data

Dec. 22, 2003 (JP) .............. 2003-423898

(51) Int. Cl.
*A61B 6/03* (2006.01)
(52) U.S. Cl. ............................ 378/15; 378/4
(58) Field of Classification Search .............. 378/4, 378/8, 15, 25, 26, 901
See application file for complete search history.

(56) References Cited

U.S. PATENT DOCUMENTS

| | | | |
|---|---|---|---|
| 5,812,628 A * | 9/1998 | Hsieh ............................ | 378/8 |
| 5,838,756 A * | 11/1998 | Taguchi et al. ................ | 378/4 |
| 5,991,356 A | 11/1999 | Horiuchi et al. | |
| 6,061,421 A | 5/2000 | Hagiwara | |
| 6,243,437 B1 * | 6/2001 | Hu et al. ....................... | 378/8 |
| 6,301,325 B1 | 10/2001 | Besson et al. | |
| 6,442,228 B1 | 8/2002 | Woloschek et al. | |
| 6,445,764 B2 | 9/2002 | Gohno et al. | |
| 6,463,118 B2 | 10/2002 | Besson | |
| 6,490,333 B1 * | 12/2002 | Hsieh ............................ | 378/4 |
| 6,526,117 B1 * | 2/2003 | Okerlund et al. ............... | 378/8 |
| 6,539,074 B1 | 3/2003 | Yavuz et al. | |
| 6,650,727 B2 | 11/2003 | Kuroda | |
| 6,744,844 B2 | 6/2004 | Horiuchi | |
| 6,795,522 B2 | 9/2004 | Nishide et al. | |
| 7,313,216 B2 * | 12/2007 | Nishide et al. ................ | 378/15 |
| 2002/0118790 A1 * | 8/2002 | Pan et al. ...................... | 378/8 |
| 2003/0031290 A1 * | 2/2003 | Sugihara et al. ............... | 378/15 |
| 2003/0063786 A1 * | 4/2003 | Nishide ...................... | 382/131 |

FOREIGN PATENT DOCUMENTS

| | | |
|---|---|---|
| EP | 1530163 A2 | 5/2005 |
| EP | 1542166 A1 | 6/2005 |
| JP | 2001145621 A * | 5/2001 |
| JP | 2002-147061 | 5/2002 |

(Continued)

OTHER PUBLICATIONS

USPTO 07-3532 dated Apr. 2007, English translation of JP2003-334188 published Nov. 25, 2003.*

(Continued)

*Primary Examiner*—Edward J Glick
*Assistant Examiner*—John M Corbett
(74) *Attorney, Agent, or Firm*—Armstrong Teasdale LLP

(57) ABSTRACT

A method of producing CT images at a plurality of positions in phase, wherein data are collected by an axial or helical scan using a multi-row detector, and a plurality of CT images at different slice positions are produced from the data collected by one axial or helical scan.

19 Claims, 10 Drawing Sheets

FOREIGN PATENT DOCUMENTS

| | | |
|---|---|---|
| JP | 2002-147231 | 5/2002 |
| JP | 2002209884 | 7/2002 |
| JP | 2002-235561 | 8/2002 |
| JP | 2002-235562 | 8/2002 |
| JP | 2002-267833 | 9/2002 |
| JP | 2002-322756 | 11/2002 |
| JP | 2002-338947 | 11/2002 |
| JP | 2003000581 | 1/2003 |
| JP | 2003-159244 | 6/2003 |
| JP | 2003159244 A * | 6/2003 |
| JP | 2003-334188 | 11/2003 |

OTHER PUBLICATIONS

Turbell, Cone-Beam Reconstruction Using Filtered Backprojection, 2001, Linkoping Studies in Science and Technology Dissertation No. 672, ISBN 91-7219-919-9, pp. 5-9 and 35-47.*

Barrett et al.,Cardiac CT Scanning: ImPACT Special Interest Report, 2003, ISBN 1 84182 746 0.*

European Search Report; Munich; Sep. 27, 2005; Application No. 042579863.2-2218 PCT; Reference 158041/10487; 3 pgs.

I. A. Hein et al.; Double-Centering Method for Increasing Efficiency of Cone-Beam X-Ray CT Reconstruction; BNSDOCID:XP2278355A; 2002; pp. 1727-1731.

* cited by examiner

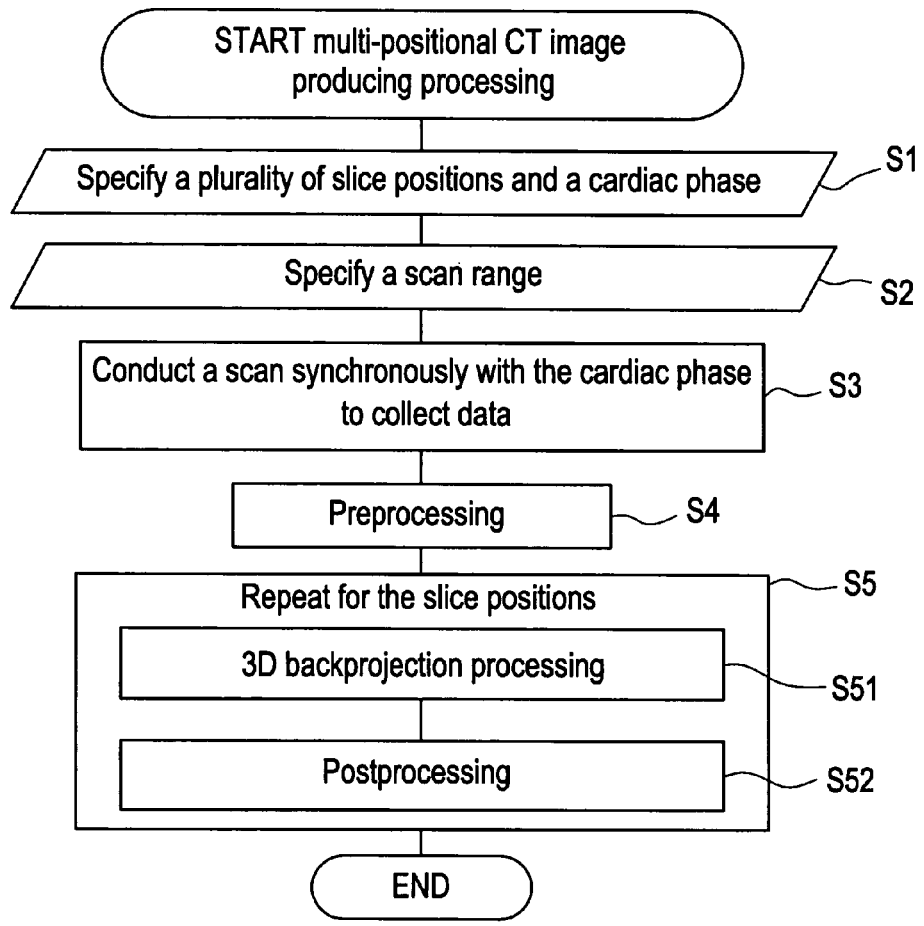

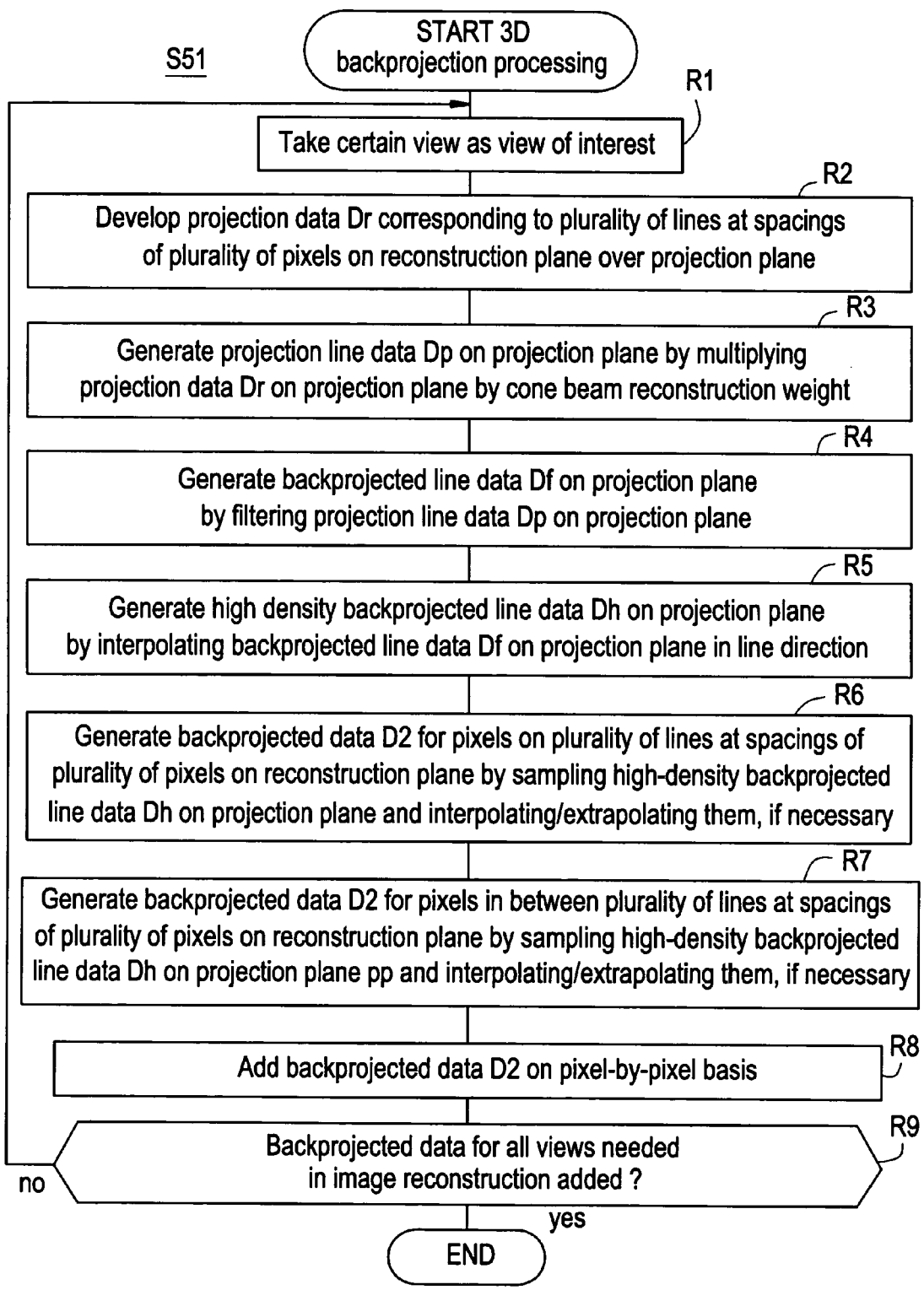

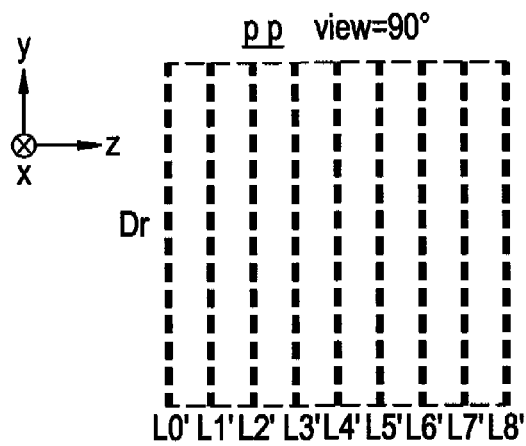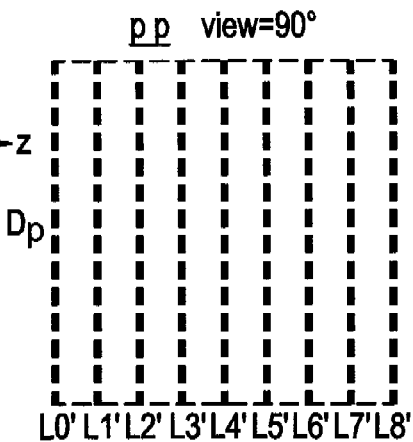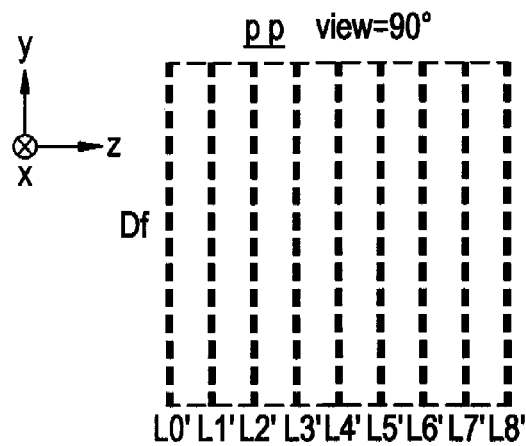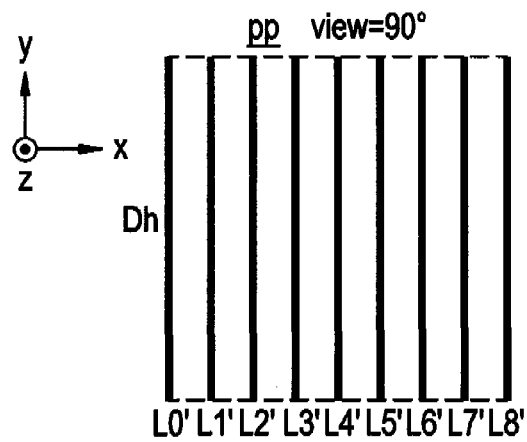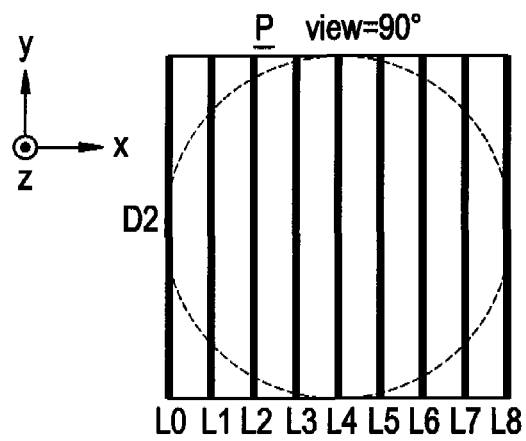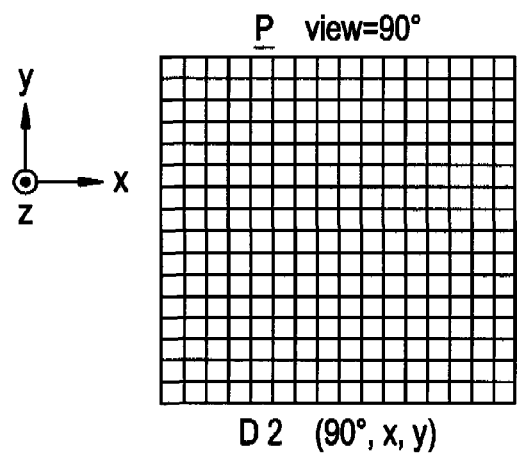

ated by United States Patent

MULTI-POSITIONAL CT IMAGE PRODUCING METHOD AND X-RAY CT APPARATUS

CROSS REFERENCE TO RELATED APPLICATIONS

This application claims the benefit of Japanese Application No. 2003-423898 filed Dec. 22, 2003.

BACKGROUND OF THE INVENTION

The present invention relates to a multi-positional CT (computed tomography) image producing method and an X-ray CT apparatus, and more particularly to a CT image producing method and an X-ray CT apparatus capable of producing CT images at a plurality of positions in phase.

A conventional technique for producing CT images at a plurality of slice positions by an axial scan comprises, for each slice position, conducting an axial scan with the slice position registered with a central detector row of a multi-row detector, collecting a data set in a required view range at the central detector row, reconstructing a CT image from the data set, and repeating these steps for the plurality of slice positions.

Moreover, a technique for producing CT images at a plurality of slice positions by a helical scan comprises, for each slice position, conducting a helical scan with the center of a scanned range registered with the slice position, collecting a data set in a required view range, reconstructing a CT image from the data set, and repeating these steps for the plurality of slice positions.

On the other hand, there is known an image reconstruction method and an X-ray CT apparatus for conducting a scan while rotating an X-ray tube and a multi-row detector around a subject to be imaged to collect data, generating a data set in a predetermined view range by extracting data of projection points formed by projecting pixels on a reconstruction plane onto a plane of the multi-row detector in a direction of X-ray transmission, and producing a CT image based on the data set (for example, see Patent Document 1).

Furthermore, there is known a three-dimensional backprojection method comprising: extracting projection data corresponding to a projection line(s) formed by projecting one line or a plurality of parallel lines at spacings of a plurality of pixels on an image reconstruction plane onto a plane of a multi-row detector in a direction of X-ray transmission; generating projection line data by multiplying the extracted projection data by a cone beam reconstruction weight; generating backprojected line data by filtering the projection line data; determining backprojected pixel data of each pixel on the reconstruction field based on the backprojected line data; and determining backprojected data by adding the backprojected pixel data on a pixel-by-pixel basis for all views used in image reconstruction (for example, see Patent Document 2).

[Patent Document 1] Japanese Patent Application Laid Open No. 2003-159244.

[Patent Document 2] Japanese Patent Application Laid Open No. 2003-334188.

When a data set in a required view range is collected by an axial or helical scan at every slice position as in the conventional techniques, the phase at which the data sets are collected differs among the slice positions. That is, CT images at a plurality of slice positions have different phases.

However, in the case of making a comparative study of CT images taken through a plurality of slice positions of a heart, for example, the different phases among the CT images pose a problem of inconvenience.

SUMMARY OF THE INVENTION

It is therefore an object of the present invention to provide a CT image producing method and an X-ray CT apparatus capable of producing CT images at a plurality of positions in phase.

In its first aspect, the present invention provides a multi-positional CT image producing method characterized in comprising: collecting data in a predetermined scan range by a scan while making a relative rotation of at least one of an X-ray tube and a multi-row detector around a subject to be imaged or while making the relative rotation and a relative rectilinear motion of the X-ray tube and multi-row detector with respect to the subject to be imaged; extracting data of detector rows corresponding to reconstruction planes at a plurality of positions to generate respective data sets for the reconstruction planes in a predetermined view range; and producing respective CT images of the reconstruction planes based on said data sets.

As used herein, the phrase "relative rotation" includes: for a subject to be imaged placed in between the X-ray tube and multi-row detector, rotating at least one of the X-ray tube and multi-row detector around the subject to be imaged without rotating the subject to be imaged; rotating the subject to be imaged around its axis without rotating the X-ray tube and multi-row detector; and rotating the subject to be imaged around its axis and rotating at least one of the X-ray tube and multi-row detector around the subject to be imaged.

As used herein, the phrase "relative rectilinear motion" includes: for a subject to be imaged placed in between the X-ray tube and multi-row detector, rectilinearly moving the subject to be imaged (or the table on which the subject to be imaged is laid) without rectilinearly moving the X-ray tube and multi-row detector; rectilinearly moving the X-ray tube and multi-row detector without rectilinearly moving the subject to be imaged (or the table on which the subject to be imaged is laid); and rectilinearly moving the subject to be imaged (or the table on which the subject to be imaged is laid) and rectilinearly moving the X-ray tube and multi-row detector.

According to the multi-positional CT image producing method of the first aspect, since a plurality of CT images at different slice positions are produced from data collected by one axial scan or helical scan using a multi-row detector, the plurality of CT images can be made in phase.

In its second aspect, the present invention provides a multi-positional CT image producing method characterized in comprising: collecting data in a predetermined scan range by a scan while making a relative rotation of at least one of an X-ray tube and a multi-row detector around a subject to be imaged or while making the relative rotation and a relative rectilinear motion of the X-ray tube and multi-row detector with respect to the subject to be imaged; extracting data at projection points formed by projecting pixels on reconstruction planes at a plurality of positions onto a plane of the multi-row detector in a direction of X-ray transmission to generate respective data sets for the reconstruction planes in a predetermined view range; and producing respective CT images of the reconstruction planes based on said data sets.

According to the multi-positional CT image producing method of the second aspect, since a plurality of CT images at different slice positions are produced from data collected by one axial scan or helical scan using a multi-row detector, the plurality of CT images can be made in phase. Moreover, since the CT images are produced by extracting data of detector rows and channels onto which an X-ray beam passing through the pixels on the reconstruction planes impinges, cone angle artifacts are reduced.

In its third aspect, the present invention provides the multi-positional CT image producing method having the aforementioned configuration, characterized in comprising: producing the CT images by a three-dimensional image reconstruction technique.

In this configuration, for the three-dimensional image reconstruction technique, the Feldkamp method and the weighted Feldkamp method are known.

According to the multi-positional CT image producing method of the third aspect, since image reconstruction is performed according to a three-dimensional image reconstruction technique, cone angle artifacts are reduced.

In its fourth aspect, the present invention provides the multi-positional CT image producing method having the aforementioned configuration, characterized in that said three-dimensional image reconstruction technique is a three-dimensional backprojection method comprising: extracting projection data corresponding to a projection line(s) formed by projecting one line or a plurality of parallel lines at spacings of a plurality of pixels on a reconstruction plane onto a plane of the multi-row detector in a direction of X-ray transmission; generating projection line data by multiplying said extracted projection data by a cone beam reconstruction weight; generating backprojected line data by filtering said projection line data; determining backprojected pixel data of each pixel on the reconstruction field based on said backprojected line data; and determining backprojected data by adding the backprojected pixel data on a pixel-by-pixel basis for all views used in image reconstruction.

According to the X-ray CT imaging method of the fourth aspect, since the three-dimensional image reconstruction technique as described in Patent Document 2 is employed, the volume of calculation can be significantly reduced.

In its fifth aspect, the present invention provides the multi-positional CT image producing method having the aforementioned configuration, characterized in that: representing a direction perpendicular to a plane of rotation of the X-ray tube and multi-row detector or a direction of rectilinear motion in a helical scan as z-direction, a direction of the center axis of the X-ray beam at a view angle view=0° as y-direction, and a direction orthogonal to the z- and y-directions as x-direction, the line direction is defined as the x-direction for $-45°\leq view<45°$ or a view angle range mainly including the range and also including its vicinity and $135°\leq view<225°$ or a view angle range mainly including the range and also including its vicinity, and the line direction is defined as the y-direction for $45°\leq view<135°$ or a view angle range mainly including the range and also including its vicinity and $225°\leq view<315°$ or a view angle range mainly including the range and also including its vicinity.

In this configuration, view=$-45°$ and view=$315°$ are actually equal and represent the same view angle, although they are differently denoted for convenience of expression.

When a line on a reconstruction plane is projected in the direction of X-ray transmission, accuracy increases for an angle between the line and direction of X-ray transmission closer to 90°, and decreases for the angle closer to 0°.

According to the CT image producing method of the fifth aspect, since the angle between the line and direction of X-ray transmission is no less than about 45°, accuracy reduction can be prevented.

In its sixth aspect, the present invention provides the multi-positional CT image producing method having the aforementioned configuration, characterized in that: said scan range is a rotation angle range of at least "180°+fan beam angle."

According to the multi-positional CT image producing method of the sixth aspect, data in a minimum view range required for reconstruction of a CT image is secured.

In its seventh aspect, the present invention provides the multi-positional CT image producing method having the aforementioned configuration, characterized in that: said view range is a rotation angle range of "180°+fan beam angle."

According to the multi-positional CT image producing method of the seventh aspect, since the view range of the data set used in reconstruction of a CT image is small, temporal resolution is improved.

In its eighth aspect, the present invention provides the multi-positional CT image producing method having the aforementioned configuration, characterized in that: phase of motion of the subject to be imaged is detected based on cardiographic or respiratory signals.

According to the multi-positional CT image producing method of the eighth aspect, a CT image can be produced at a desired phase of the heart or lungs.

In its ninth aspect, the present invention provides an X-ray CT apparatus characterized in comprising: an X-ray tube; a multi-row detector; scanning means for collecting data in a predetermined scan range by a scan while making a relative rotation of at least one of said X-ray tube and said multi-row detector around a subject to be imaged or making the relative rotation and a relative rectilinear motion of said X-ray tube and said multi-row detector with respect to the subject to be imaged; data extracting means for extracting data of detector rows corresponding to reconstruction planes at a plurality of positions to generate respective data sets for the reconstruction planes in a predetermined view range; and image reconstruction means for producing respective CT images of the reconstruction planes based on said data sets.

According to the X-ray CT apparatus of the ninth aspect, the multi-positional CT image producing method of the first aspect can be suitably implemented.

In its tenth aspect, the present invention provides an X-ray CT apparatus characterized in comprising: an X-ray tube; a multi-row detector; scanning means for collecting data in a predetermined scan range by a scan while making a relative rotation of at least one of said X-ray tube and said multi-row detector around a subject to be imaged or making the relative rotation and a relative rectilinear motion of said X-ray tube and said multi-row detector with respect to the subject to be imaged; data extracting means for extracting data at projection points formed by projecting pixels on reconstruction planes at a plurality of positions onto a plane of the multi-row detector in a direction of X-ray transmission to generate respective data sets for the reconstruction planes in a predetermined view range; and image reconstruction means for producing respective CT images of the reconstruction planes based on said data sets.

According to the X-ray CT apparatus of the tenth aspect, the multi-positional CT image producing method of the second aspect can be suitably implemented.

In its eleventh aspect, the present invention provides the X-ray CT apparatus having the aforementioned configuration, characterized in: producing the CT images by a three-dimensional image reconstruction technique.

According to the X-ray CT apparatus of the eleventh aspect, the multi-positional CT image producing method of the third aspect can be suitably implemented.

In its twelfth aspect, the present invention provides the X-ray CT apparatus having the aforementioned configuration, characterized in that said three-dimensional image reconstruction technique is a three-dimensional backprojection method comprising: extracting projection data corresponding to a projection line(s) formed by projecting one line or a plurality of parallel lines at spacings of a plurality of pixels on a reconstruction plane onto a plane of the multi-row detector in a direction of X-ray transmission; generating projection line data by multiplying said extracted projection data by a cone beam reconstruction weight; generating backprojected line data by filtering said projection line data; determining backprojected pixel data of each pixel on the reconstruction field based on said backprojected line data; and determining backprojected data by adding the backprojected pixel data on a pixel-by-pixel basis for all views used in image reconstruction.

According to the X-ray CT apparatus of the twelfth aspect, the multi-positional CT image producing method of the fourth aspect can be suitably implemented.

In its thirteenth aspect, the present invention provides the X-ray CT apparatus having the aforementioned configuration, characterized in that: representing a direction perpendicular to a plane of rotation of the X-ray tube and multi-row detector or a direction of rectilinear motion in a helical scan as z-direction, a direction of the center axis of the X-ray beam at a view angle view=0° as y-direction, and a direction orthogonal to the z- and y-directions as x-direction, the line direction is defined as the x-direction for −45°≦view<45° or a view angle range mainly including the range and also including its vicinity and 135°≦view<225° or a view angle range mainly including the range and also including its vicinity, and the line direction is defined as the y-direction for 45°≦view<135° or a view angle range mainly including the range and also including its vicinity and 225°≦view<315° or a view angle range mainly including the range and also including its vicinity.

According to the X-ray CT apparatus of the thirteenth aspect, the multi-positional CT image producing method of the fifth aspect can be suitably implemented.

In its fourteenth aspect, the present invention provides the X-ray CT apparatus having the aforementioned configuration, characterized in that: said scan range is a rotation angle range of at least "180°+fan beam angle."

According to the X-ray CT apparatus of the fourteenth aspect, the multi-positional CT image producing method of the sixth aspect can be suitably implemented.

In its fifteenth aspect, the present invention provides the X-ray CT apparatus having the aforementioned configuration, characterized in that: said view range is a rotation angle range of "180°+fan beam angle."

According to the X-ray CT apparatus of the fifteenth aspect, the multi-positional CT image producing method of the seventh aspect can be suitably implemented.

In its sixteenth aspect, the present invention provides the X-ray CT apparatus having the aforementioned configuration, characterized in that phase of motion of the subject to be imaged is detected based on cardiographic or respiratory signals.

According to the X-ray CT apparatus of the sixteenth aspect, the multi-positional CT image producing method of the eighth aspect can be suitably implemented.

According to the multi-positional CT image producing method and X-ray CT apparatus of the present invention, CT images at a plurality of positions can be produced in phase.

The multi-positional CT image producing method and X-ray CT apparatus of the present invention may be used in producing CT images of a plurality of cross sections and at the same phase of the heart.

Further objects and advantages of the present invention will be apparent from the following description of the preferred embodiments of the invention as illustrated in the accompanying drawings.

BRIEF DESCRIPTION OF THE DRAWINGS

FIG. 4 is a flow chart showing multi-positional CT image producing processing.

FIG. 5 is an explanatory diagram showing a format for storing collected data.

FIG. 6 is a flow chart showing details of three-dimensional image reconstruction processing.

FIG. 15 is a conceptual diagram showing projection data Dr on lines on the detector plane at a view angle view=90° projected onto a projection plane.

FIG. 16 is a conceptual diagram showing projection line data Dp obtained by multiplying the projection data Dr on the projection plane pp at the view angle view=90° by a cone beam reconstruction weight.

FIG. 17 is a conceptual diagram showing backprojected line data Df obtained by filtering the projection line data Dp on the projection plane pp at the view angle view=90°.

FIG. 18 is a conceptual diagram showing high density backprojected line data Dh obtained by interpolating the backprojected line data Df on the projection plane pp at the view angle view=90°.

FIG. 19 is a conceptual diagram showing backprojected pixel data D2 obtained by developing the high density backprojected line data Dh on the projection plane pp at the view angle view=90° over lines on a reconstruction plane.

FIG. 20 is a conceptual diagram showing backprojected pixel data D2 obtained by developing the high density backprojected line data Dh on the projection plane pp at the view angle view=90° in between the lines on the reconstruction plane.

DETAILED DESCRIPTION OF THE INVENTION

The present invention will now be described in more detail with reference to embodiments shown in the accompanying drawings. It should be noted that the present invention is not limited to the embodiments.

EXAMPLE 1

Figure 1:
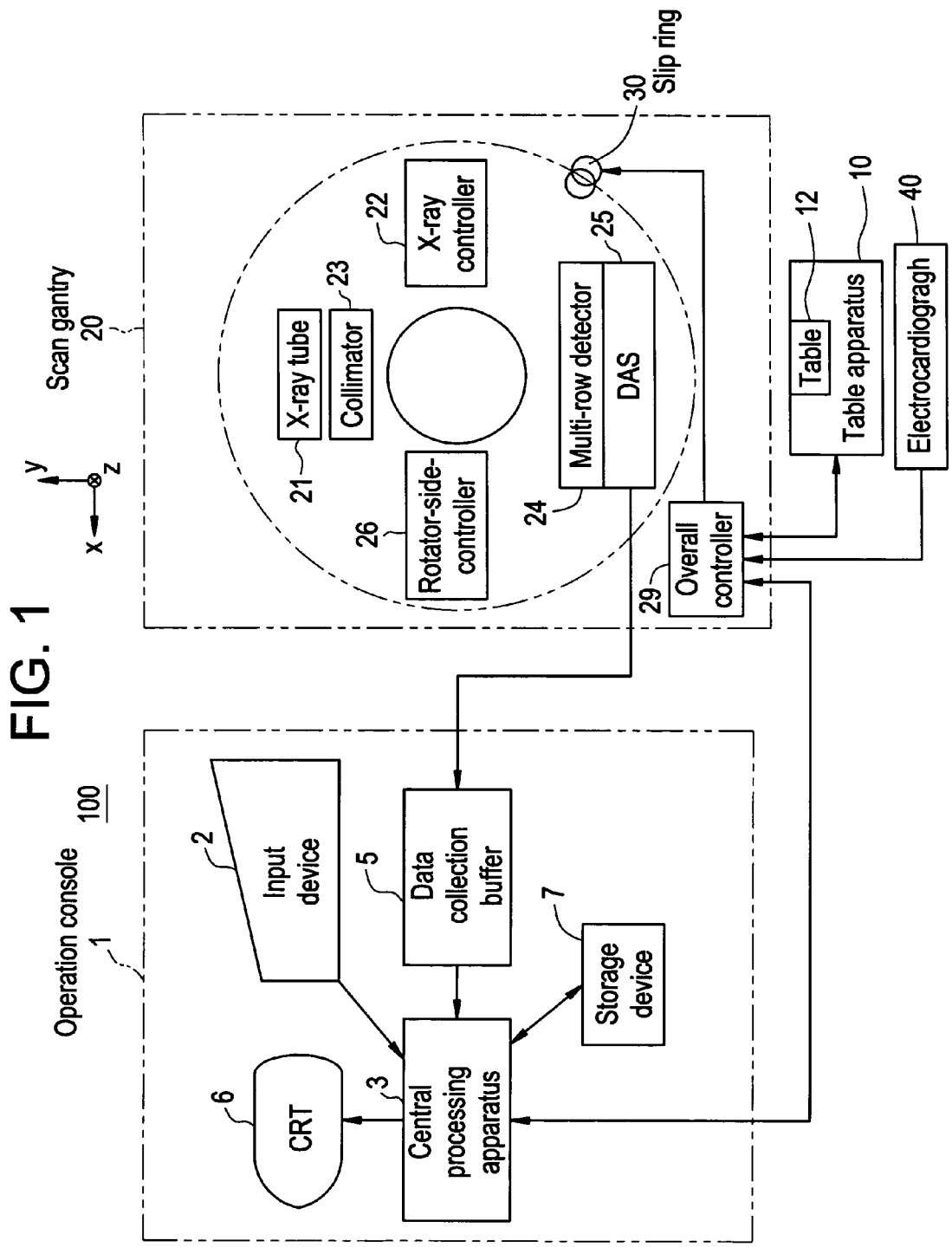
FIG. 1 is a block configuration diagram showing an X-ray CT apparatus of Example 1.

FIG. 1 is a block configuration diagram showing an X-ray CT apparatus 100 of Example 1.

The X-ray CT apparatus 100 comprises an operation console 1, a table apparatus 10, a scan gantry 20, and an electrocardiograph 40.

The operation console 1 comprises an input device 2 for accepting inputs by a human operator, a central processing apparatus 3 for executing scan control processing, image reconstruction processing etc., a data collection buffer 5 for collecting data acquired at the scan gantry 20, a CRT 6 for displaying a produced CT image, and a storage device 7 for storing programs, data, and X-ray CT images.

The table apparatus 10 comprises a table 12 for laying thereon a subject to be imaged and transporting the subject into/out of a bore (cavity portion) of the scan gantry 20. The table 12 is vertically and horizontally/rectilinearly moved by a motor incorporated in the table apparatus 10.

The scan gantry 20 comprises an X-ray tube 21, an X-ray controller 22, a collimator 23, a multi-row detector 24, a DAS (data acquisition system) 25, a rotator-side controller 26 for controlling the X-ray controller 22, collimator 23 and DAS 25, an overall controller 29 for communicating control signals etc. with the operation console 1 and imaging table 10, and a slip ring 30.

The electrocardiograph 40 detects cardiographic signals of the subject to be imaged.

Figure 2:
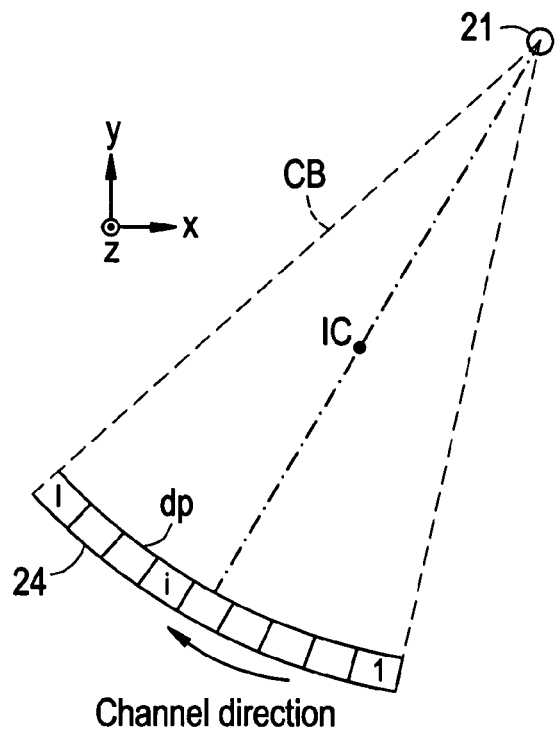
FIG. 2 is an explanatory diagram showing a rotation of an X-ray tube and a multi-row detector.
Figure 3:
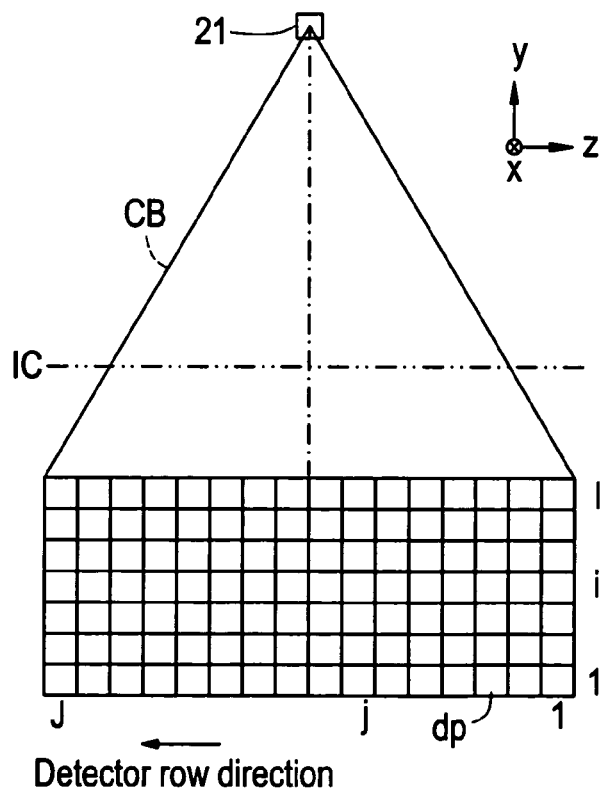
FIG. 3 is an explanatory diagram showing a cone beam.

FIGS. 2 and 3 are explanatory diagrams of the X-ray tube 21 and multi-row detector 24.

The X-ray tube 21 and multi-row detector 24 rotate around a center of rotation IC. Representing the direction of rectilinear motion of the table 12 as z-direction, a direction perpendicular to the upper surface of the table 12 as y-direction, and a direction orthogonal to the z- and y-directions as x-direction, a plane of rotation of the X-ray tube 21 and multi-row detector 24 is an x-y plane.

The X-ray tube 21 generates an X-ray beam CB generally referred to as a cone beam. When the direction of the center axis of the X-ray beam CB is parallel to the y-direction, a view angle view=0° is defined.

The multi-row detector 24 has J (e.g., J=256) detector rows. Each row has I (e.g., I=1,024) channels.

FIG. 4 is a flow chart showing multi-positional CT image producing processing.

Figure 22A:
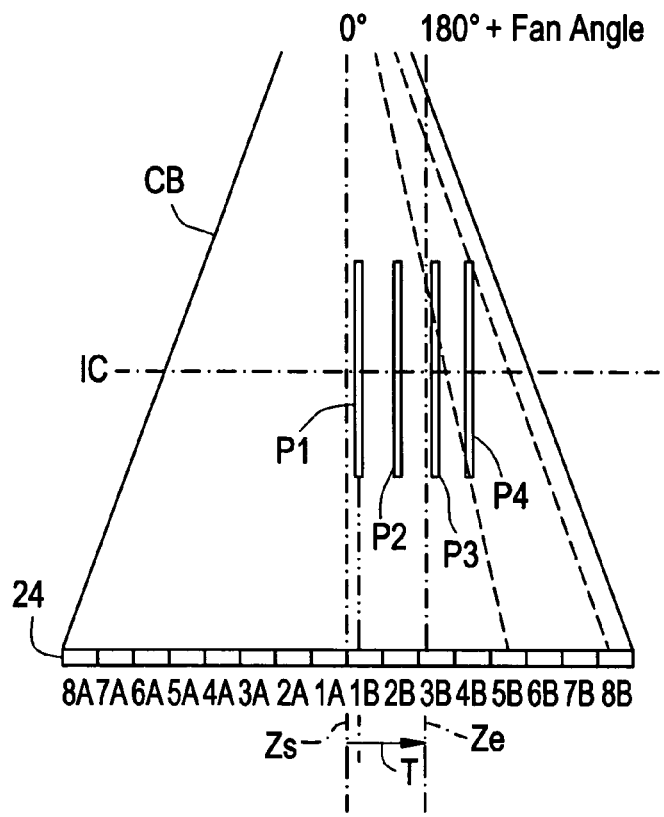
FIG. 22 is an explanatory diagram showing the relationship between a plurality of reconstruction planes and a scan range in accordance with Example 1.
Figure 22B:
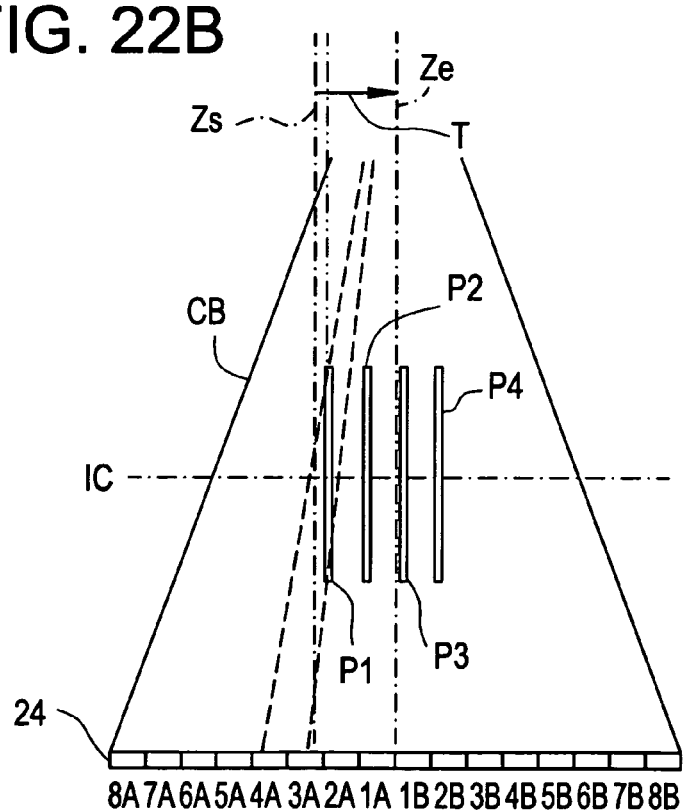

At Step S1, the operator specifies a plurality of slice positions. For example, as shown in FIG. 22, a plurality of slice positions P1, P2, P3 and P4 across the heart of the subject to be imaged are specified. Moreover, the cardiac phase at which data are desired is specified.

At Step S2, the operator specifies a scan range. For example, in an axial scan, a z-position of the center of the multi-row detector 24, a scan start angle and a scan end angle are specified. In a helical scan, a scan start point Zs and a scan end point Ze, and a scan start angle "0°" and a scan end angle "180°+fan angle" are specified, as exemplarily illustrated in FIG. 22. It should be noted that a wider scan range may be specified.

At Step S3, the X-ray CT apparatus 100 conducts a scan synchronously with the phase of cardiographic signals, and collects data.

Specifically, data D0(z, view, j, i) represented by the z-position z, view angle view, detector row index j and channel index i is collected while rotating the X-ray tube 21 and multi-row detector 24 around the subject to be imaged without rectilinearly moving the table 12, or data D0(z, view, j, i) represented by the rectilinear motion position z, view angle view, detector row index j and channel index i is collected while rotating the X-ray tube 21 and multi-row detector 24 around the subject to be imaged and rectilinearly moving the table 12. The rectilinear motion position z is obtained by an encoder counting a z-position pulse, converted into a z-coordinate at the overall controller 29, passed via the slip ring 30, and appended as z-coordinate information to the projection data from the DAS 25.

FIG. 5 shows a format of the data at a certain view angle view appended with the z-coordinate information.

At Step S4, the X-ray CT apparatus 100 applies pre-processing (offset correction, log correction, X-ray dose correction and sensitivity correction) to the data D0(z, view, j, i).

At Step S5, the X-ray CT apparatus 100 repeats Steps S51 and S52 for a plurality of slice positions.

At Step S51, the pre-processed data D0(z, view, j, i) is subjected to three-dimensional backprojection processing to determine backprojected data D3(x, y).

The three-dimensional backprojection processing at Step S51 will be discussed later with reference to FIG. 6.

At Step S52, the backprojected data D3(x, y) is subjected to post-processing to obtain a CT image.

FIG. 6 is a flow chart showing details of the three-dimensional backprojection processing (Step S51 in FIG. 4).

At Step R1, one view is taken as a view of interest in a view range needed in image reconstruction. The view range is, for example, "180°+fan angle" or "360°."

At Step R2, projection data Dr corresponding to a plurality of parallel lines at spacings of a plurality of pixels on a reconstruction plane P are extracted from among the data D0(z, view, j, i) at the view of interest.

Figure 7A:
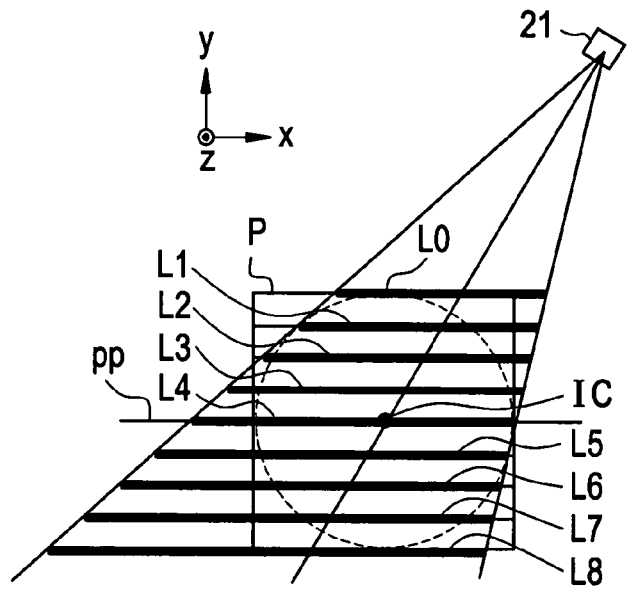
FIG. 7 is a conceptual diagram showing lines on a reconstruction plane P projected in the direction of X-ray transmission.
Figure 7B:
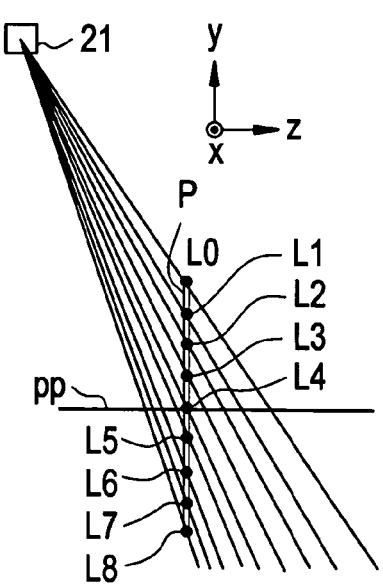

FIG. 7 exemplarily shows a plurality of parallel lines L0-L8 on the reconstruction plane P.

The number of lines is ¹⁄₆₄-½ of the maximum number of pixels in the reconstruction plane in a direction orthogonal to the lines. For example, if the number of pixels in the reconstruction plane P is 512×512, the number of lines is nine.

Moreover, the line direction is defined as the x-direction for −45°≦view<45° (or a view angle range mainly including the range and also including its vicinity) and 135°≦view<225° (or a view angle range mainly including the range and also including its vicinity). The line direction is defined as the y-direction for 45°≦view<135° (or a view angle range mainly including the range and also including its vicinity) and 225°≦view<315° (or a view angle range mainly including the range and also including its vicinity).

Furthermore, a projection plane pp is assumed to pass through the center of rotation IC and be parallel to the lines L0-L8.

Figure 8:
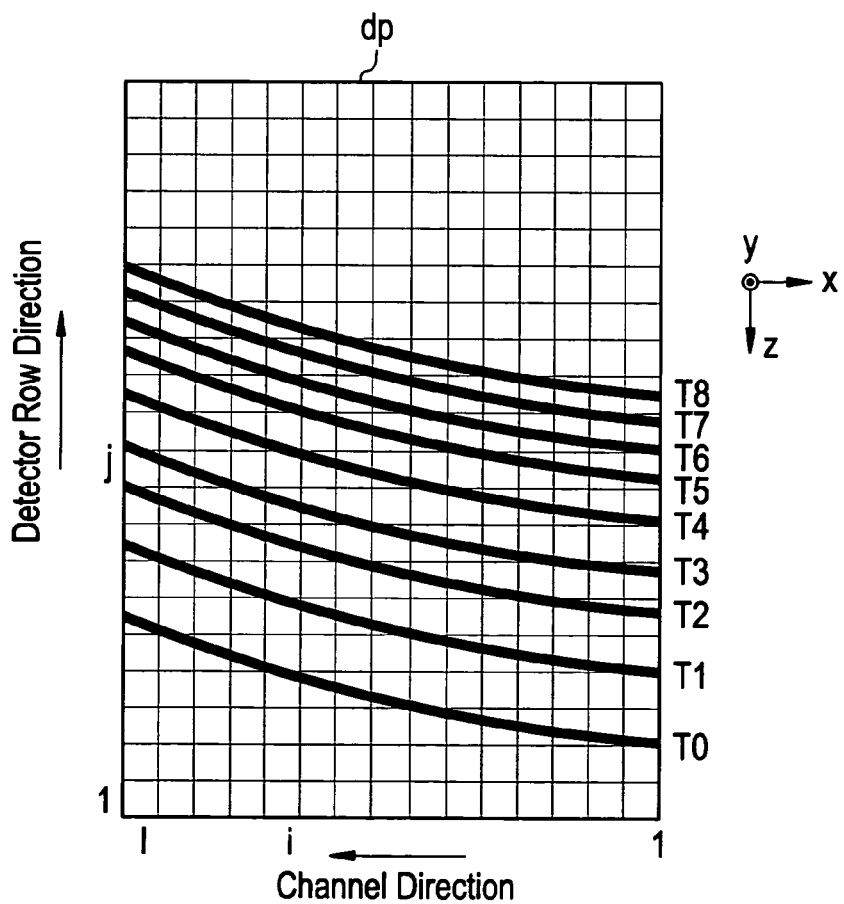
FIG. 8 is a conceptual diagram showing lines on the reconstruction plane P projected onto a detector plane.

FIG. 8 shows lines T0-T8 formed by projecting the plurality of parallel lines L0-L8 on the reconstruction plane P onto a detector plane dp in a direction of X-ray transmission.

The direction of X-ray transmission is determined based upon the geometry of the X-ray tube 21, multi-row detector 24 and lines L0-L8.

The projection data Dr corresponding to the lines L0-L8 can be obtained by extracting data at the detector row j and channel i corresponding to the lines T0-T8 projected onto the detector plane dp.

Figure 9:
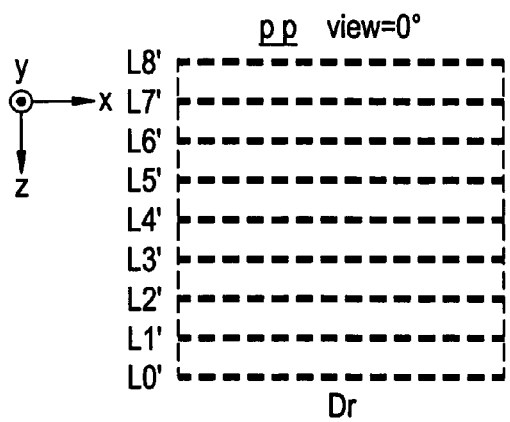
FIG. 9 is a conceptual diagram showing projection data Dr on lines on the detector plane at a view angle view=0° projected onto a projection plane.

Now lines L0'-L8' formed by projecting the lines T0-T8 onto the projection plane pp in the direction of X-ray transmission are assumed as shown in FIG. 9, and the projection data Dr are developed over the lines L0'-L8' on the projection plane pp.

Figure 10:
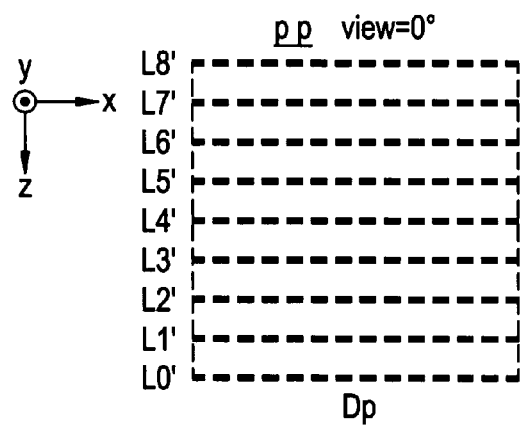
FIG. 10 is a conceptual diagram showing projection line data Dp obtained by multiplying the projection data Dr on the projection plane pp at the view angle view=0° by a cone beam reconstruction weight.

Referring again to FIG. 6, at Step R3, the projection data Dr of the lines L0'-L8' on the projection plane pp are multiplied by a cone beam reconstruction weight to generate projection line data Dp on the projection plane pp as shown in FIG. 10.

The cone beam reconstruction weight is $(r1/r0)^2$, where r0 is the distance from the focal spot of the X-ray tube 21 to the j-th detector row and the i-th channel of the multi-row detector 24 corresponding to projection data Dr, and r1 is the distance from the focal spot of the X-ray tube 21 to a point on the reconstruction plane P corresponding to the projection data Dr.

Figure 11:
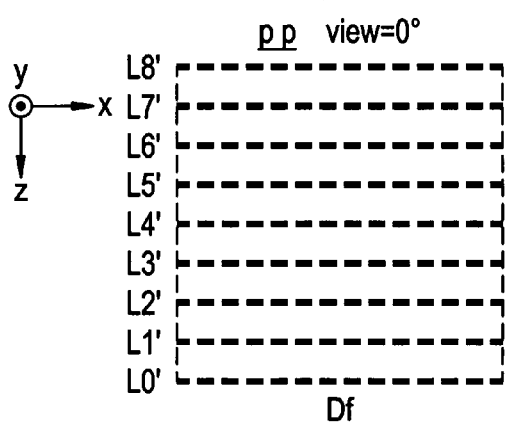
FIG. 11 is a conceptual diagram showing backprojected line data Df obtained by filtering the projection line data Dp on the projection plane pp at the view angle view=0°.

At Step R4, the projection line data Dp on the projection plane pp are filtered. Specifically, the projection line data Dp on the projection plane pp are subjected to FFT, multiplied by a filter function (reconstruction function), and subjected to inverse FFT to generate image backprojected line data Df on the projection plane pp as shown in FIG. 11.

Figure 12:
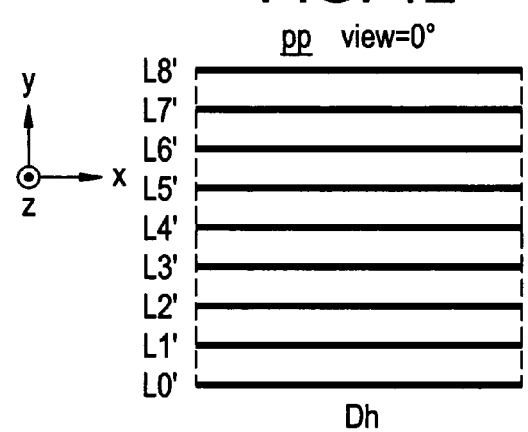
FIG. 12 is a conceptual diagram showing high density backprojected line data Dh obtained by interpolating the backprojected line data Df on the projection plane pp at the view angle view=0°.

At Step R5, the backprojected line data Df on the projection plane pp is interpolated in the line direction to generate high-density backprojected line data Dh on the projection plane pp as shown in FIG. 12.

The data density of the high-density backprojected line data Dh on the projection plane pp is 8-32 times the maximum number of pixels in the reconstruction plane P in the line direction. For example, if the factor is 16 and the number of pixels in the reconstruction plane P is 512×512, the data density is 8,192 points/line.

Figure 13:
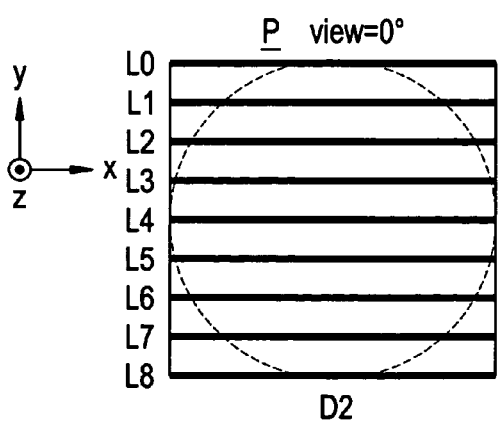
FIG. 13 is a conceptual diagram showing backprojected pixel data D2 obtained by developing the high density backprojected line data Dh on the projection plane pp at the view angle view=0° over lines on a reconstruction plane.

At Step R6, the high-density backprojected line data Dh on the projection plane pp are sampled and interpolated/extrapolated, if necessary, to generate backprojected pixel data D2 for pixels on the lines L0-L8 on the reconstruction plane P, as shown in FIG. 13.

Figure 14:
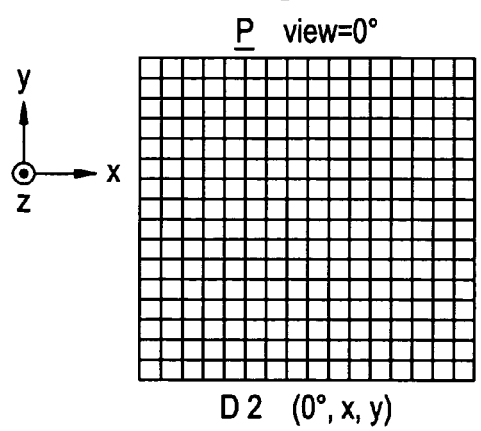
FIG. 14 is a conceptual diagram showing backprojected pixel data D2 obtained by developing the high density backprojected line data Dh on the projection plane pp at the view angle view=0° in between the lines on the reconstruction plane.

At Step R7, the high-density backprojected line data Dh are sampled and interpolated/extrapolated to generate backprojection data D2 for pixels in between the lines L0-L8, as shown in FIG. 14. Alternatively, the interpolation/extrapolation is conducted based on the backprojected pixel data D2 for pixels on the lines L0-L8 on the reconstruction plane P to generate backprojected pixel data D2 for pixels in between the lines L0-L8.

Figure 21:
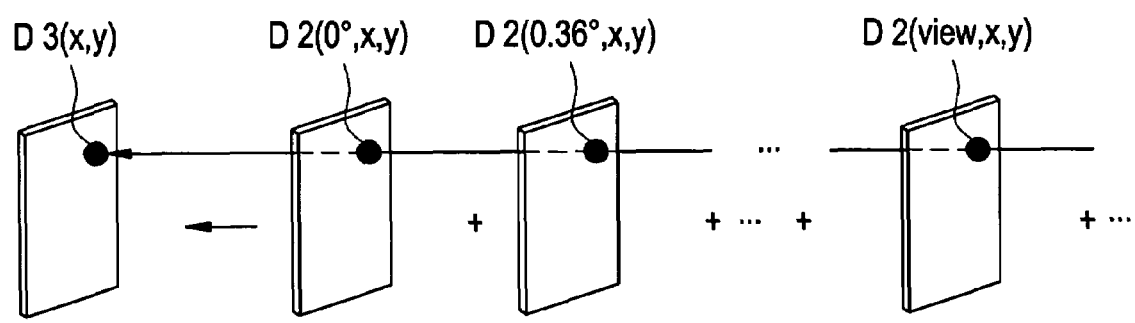
FIG. 21 is an explanatory diagram showing backprojected data D3 obtained by adding the backprojected pixel data D2 on a pixel-by-pixel basis for all views.

In FIGS. 9-14, −45°≦view<45° (or a view angle range mainly including the range and also including its vicinity) and 135°≦view<225° (or a view angle range mainly including the range and also including its vicinity) are assumed, while FIGS. 15-20 are applied for 45°≦view<135° (or a view angle range mainly including the range and also including its vicinity) and 225°≦view<315° (or a view angle range mainly including the range and also including its vicinity). Referring again to FIG. 6, at Step R8, the backprojected pixel data D2 shown in FIG. 14 or 20 are added on a pixel-by-pixel basis, as shown in FIG. 21. At Step R9, Steps R1-R8 are repeated for all views needed in image reconstruction to obtain backprojected data D3(x, y).

FIG. 22 is an explanatory diagram showing the relationship between a reconstruction plane P and a detector row in the multi-row detector 24. Data at views needed in image reconstruction of reconstruction planes P1, P2, P3 and P4 can be extracted from data of detector rows 4A-8B.

According to the X-ray CT apparatus 100 of Example 1, since CT images at a plurality of slice positions P1, P2, P3 and P4 are produced from data collected by one helical scan using the multi-row detector 24, the plurality of CT images can be made in phase.

Moreover, since the CT images are produced by extracting data of the detector rows and channels onto which an X-ray beam passing through pixels on the reconstruction planes P impinges, cone angle artifacts are reduced.

If the X-ray beam passing through pixels on the reconstruction plane P falls outside the multi-row detector 24, data of a detector row and channel closest to the X-ray beam passing through the pixels on the reconstruction plane P may be used instead.

EXAMPLE 2

The technique for image reconstruction may be a conventionally known three-dimensional image reconstruction technique according to the Feldkamp method. Moreover, three-dimensional image reconstruction techniques proposed in Japanese Patent Application Nos. 2002-147061, 2002-147231, 2002-235561, 2002-235662, 2002-267833, 2002-322756 and 2002-338947 may be employed.

EXAMPLE 3

Figure 23A:
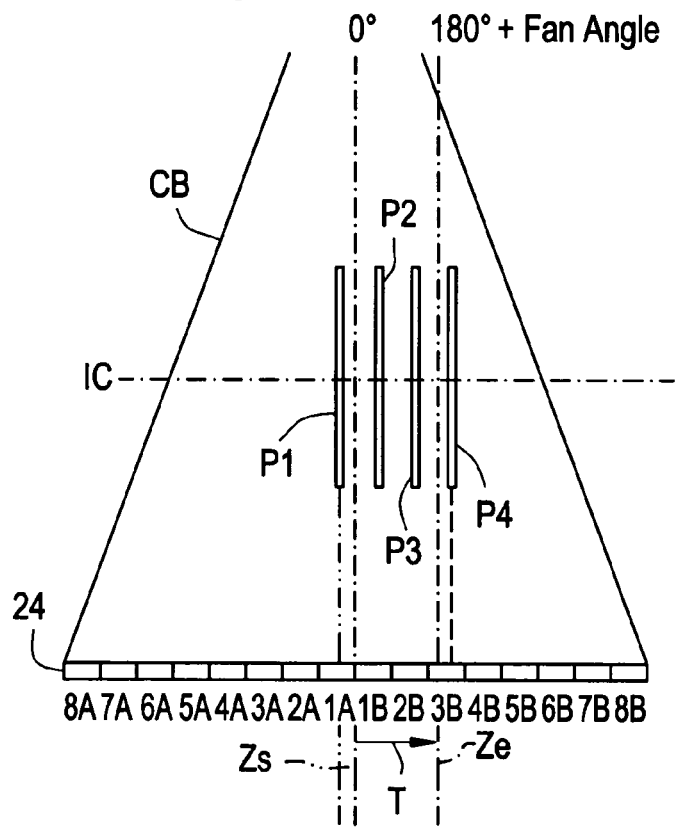
FIG. 23 is an explanatory diagram showing the relationship between a plurality of reconstruction planes and a scan range in accordance with Example 3.
Figure 23B:
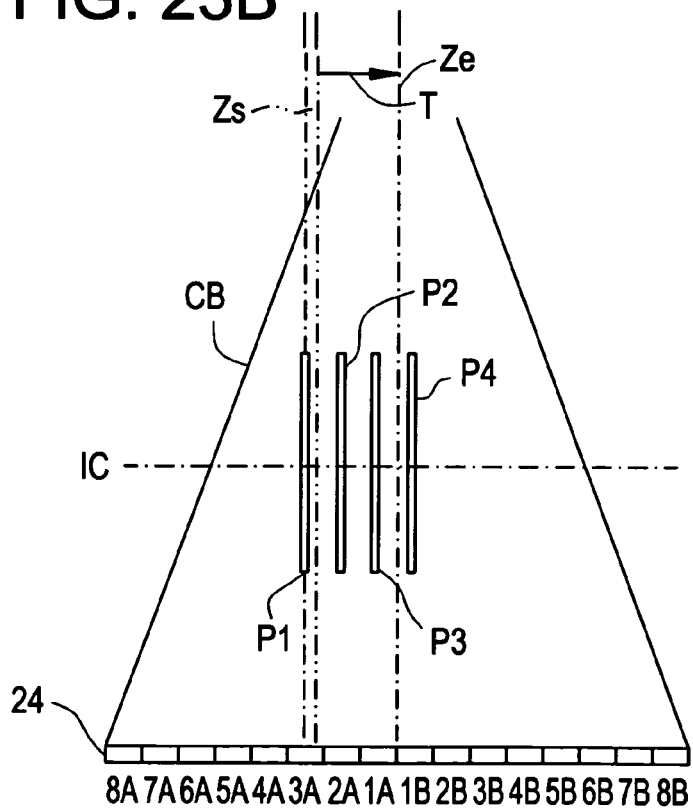

CT images may be reconstructed from data sets generated by extracting data of detector rows straight below the reconstruction planes P1, P2, P3 and P4, without respect to the direction of X-ray beam transmission, as shown in FIG. 23.

EXAMPLE 4

Data may be collected by an axial scan rather than by a helical scan.

EXAMPLE 5

The technique for image reconstruction may be a two-dimensional image reconstruction technique.

Many widely different embodiments of the invention may be configured without departing from the spirit and the scope of the present invention. It should be understood that the present invention is not limited to the specific embodiments described in the specification, except as defined in the appended claims.

What is claimed is:

1. A multi-positional computed tomography (CT) image producing method comprising the steps of:
    collecting data in a predetermined scan range using a helical scan that includes making a relative rotation of at least one of an X-ray tube and a multi-row detector around a subject to be imaged while making a relative rectilinear motion of the X-ray tube and the multi-row detector with respect to the subject to be imaged;

extracting data from detector rows corresponding to reconstruction planes at a plurality of positions to generate respective data sets for a reconstruction, wherein all of the reconstruction planes are set in such a manner that the data of the detector rows corresponding to the reconstruction planes are acquired at each view angle within a predetermined view range; and producing respective CT images of the plurality of reconstruction planes based on the data sets.

2. The multi-positional CT image producing method of claim 1, wherein producing respective CT images of the plurality of reconstruction planes further comprises producing the CT images by a three-dimensional image reconstruction technique.

3. The multi-positional CT image producing method of claim 2, wherein said three-dimensional image reconstruction technique is a three-dimensional backprojection method comprising the steps of:

extracting projection data corresponding to at least one projection line formed by projecting at least one line of a plurality of parallel lines at spacings of a plurality of pixels on a first reconstruction plane of the plurality of reconstruction planes onto a plane of the multi-row detector in a direction of X-ray transmission;

generating projection line data by multiplying said extracted projection data by a cone beam reconstruction weight;

generating backprojected line data by filtering said projection line data;

determining backprojected pixel data of each pixel of the plurality of pixels on the first reconstruction plane based on said backprojected line data; and determining backprojected data by adding the backprojected pixel data on a pixel-by-pixel basis for all views used in image reconstruction.

4. The multi-positional CT image producing method of claim 3 further comprising:

defining a line direction as an x-direction for a view angle of one of approximately −45°≦view<approximately 45° and approximately 135°≦view<approximately 225°; and defining the line direction as a y-direction for a view angle of one of approximately −45°≦view<approximately 135°and approximately 225°≦view<approximately 315°, wherein a direction perpendicular to a plane of rotation of the X-ray tube and multi-row detector or a direction of rectilinear motion in a helical scan as a z-direction, a direction of a center axis of an X-ray beam at a view angle of 0° as the y-direction, and a direction orthogonal to the z-direction and the y-direction as the x-direction.

5. The multi-positional CT image producing method of claim 1, wherein said scan range is a rotation angle range of at least 180°+fan beam angle.

6. The multi-positional CT image producing method of claim 1, wherein said view range is a rotation angle range of 180°+fan beam angle.

7. The multi-positional CT image producing method of claim 1, wherein phase of motion of the subject to be imaged is detected based on cardiographic or respiratory signals.

8. The multi-positional CT image producing method of claim 1, wherein extracting data further comprises extracting data of detector rows corresponding to the plurality of reconstruction planes at a plurality of positions to generate projection points formed by projecting pixels on the plurality of reconstruction planes onto a plane of the multi-row detector in a direction of X-ray transmission to generate the respective data sets for each reconstruction plane in the predetermined view range.

9. The multi-positional CT image producing method of claim 1, wherein producing respective CT images further comprises projecting at least one respective data set onto a detector plane.

10. The multi-positional CT image producing method of claim 9, wherein producing respective CT images further comprises projecting the at least one detector plane data set onto a projection plane.

11. The multi-positional CT image producing method of claim 10, wherein producing respective CT images further comprises backprojecting the at least one projection plane data set to produce at least one backprojected data set, the at least one backprojected data set comprising pixel data on the reconstruction plane.

12. The multi-positional CT image producing method of claim 1, wherein producing respective CT images further comprises producing a plurality of CT images at a plurality of slice positions, wherein the plurality of CT images are in phase.

13. An X-ray computed tomography (CT) apparatus comprising:

an X-ray tube;

a multi-row detector;

a scanning device for collecting data in a predetermined scan range using a helical scan that includes making a relative rotation of at least one of said X-ray tube and said multi-row detector around a subject to be imaged while making a relative rectilinear motion of said X-ray tube and said multi-row detector with respect to the subject to be imaged;

a data extracting device for extracting data from detector rows corresponding to reconstruction planes at a plurality of positions to generate respective data sets for a reconstruction, wherein all of the reconstruction planes are set in such a manner that the data of the detector rows corresponding to the reconstruction planes are acquired at each view angle within a predetermined view range; and an image reconstruction device for producing respective CT images of the reconstruction planes based on said data sets.

14. The X-ray CT apparatus of claim 13, wherein the image reconstruction device produces the CT images by a three-dimensional image reconstruction technique.

15. The X-ray CT apparatus of claim 14, wherein said three-dimensional image reconstruction technique is a three-dimensional backprojection method comprising the steps of:

extracting projection data corresponding to at least one projection line formed by projecting at least one line of a plurality of parallel lines at spacings of a plurality of pixels on a first reconstruction plane of the plurality of reconstruction planes onto a plane of the multi-row detector in a direction of X-ray transmission;

generating projection line data by multiplying said extracted projection data by a cone beam reconstruction weight;

generating backprojected line data by filtering said projection line data;

determining backprojected pixel data of each pixel on the reconstruction field based on said backprojected line data; and determining backprojected data by adding the backprojected pixel data on a pixel-by-pixel basis for all views used in image reconstruction.

16. The X-ray CT apparatus of claim 15, wherein a line direction is defined as an x-direction for a view angle of one of approximately −45°≦view<approximately 45° and approximately 135°≦view<approximately 225°, and wherein the line direction is defined as a y-direction for a view angle of one of approximately 45°≦view<approximately 135° and approximately 225°≦view<approximately 315°, a direction perpendicular to a plane of rotation of the X-ray tube and the multi-row detector or a direction of rectilinear motion in a helical scan as z-direction, a direction of a center axis of an X-ray beam at a view angle of 0° as y-direction, and a direction orthogonal to the z-direction and the y-direction as the x-direction.

17. The X-ray CT apparatus of claim 13, wherein said scan range is a rotation angle range of at least 180°+fan beam angle.

18. The X-ray CT apparatus of claim 13, wherein said view range is a rotation angle range of 180°+fan beam angle.

19. The X-ray CT apparatus of claim 13, wherein phase of motion of the subject to be imaged is detected based on cardiographic or respiratory signals.

* * * * *